United States Patent [19]

Egidio et al.

[11] Patent Number: 5,236,910
[45] Date of Patent: Aug. 17, 1993

[54] USE OF GLYCOSAMINOGLYCANS IN THE TREATMENT OF DIABETIC NEPHROPATHY AND DIABETIC NEUROPATHY

[75] Inventors: Marchi Egidio, Bologna; Tamagnone Gianfranco, Casalecchir di Reno, both of Italy

[73] Assignee: ALFA Wassermann S.p.A., Alanno, Italy

[21] Appl. No.: 871,048

[22] Filed: Apr. 20, 1992

[30] Foreign Application Priority Data

May 17, 1991 [IT] Italy .............................. 000163 A/91

[51] Int. Cl.$^5$ .......................................... A61K 31/725
[52] U.S. Cl. ........................................ 514/56; 514/53; 514/54; 514/866
[58] Field of Search ...................... 514/53, 54, 56, 866

[56] References Cited

PUBLICATIONS

Chemical Abstracts 113:71329b, 1990.

Primary Examiner—Leonard Schenkman
Attorney, Agent, or Firm—Bucknam and Archer

[57] ABSTRACT

The object of the present invention is the manufacture of a medicine for the use of glycosaminoglycans in the prevention and treatment of some pathologies caused by diabetes, like diabetic nephropathy and diabetic neuropathy.

The effectiveness of glycosaminoglycans in the prevention and treatment of said pathologies has been shown by the treatment with some glycosaminoglycans of male albino rats made diabetic by treatment with streptozotocin or alloxan and by the subsequent determination of morphological and clinical parameters like the thickness of the glomerular basal membrane, the number of the glomerular anionic charges and albuminuria in case of diabetic nephropathy, and like the levels of substance P and Met-Enkephalin in some intestinal zones, like duodenum and jejunum, in case of diabetic neuropathy.

8 Claims, No Drawings

USE OF GLYCOSAMINOGLYCANS IN THE TREATMENT OF DIABETIC NEPHROPATHY AND DIABETIC NEUROPATHY

BACKGROUND OF THE INVENTION

The use of glycosaminoglycans, and particularly of heparins, in anticoagulant and antithrombotic therapies is well known, while their use in the treatment of the collateral pathologies of diabetes, like diabetic nephropathy and diabetic neuropathy, is unknown.

Kanwar Y. S. et al., Sem. Nephrol., 5, 307, (1985) and Groggel G. C. et al., Kidney Int., 33, 517, (1988), recently produced evidence of the probable role of glycosaminoglycans in helping the integrity and the functioning of the renal cells.

Moreover, Canfield J. P. et al., Lab. Invest., 39, 505, (1978), previously showed a decrease of glycosaminoglycans of membrane in many conditions of nephropathy, while Baggio B. et al., Nephron., 43, 187, (1986) showed this decrease through an increased urinary elimination of glycosaminoglycans in diabetic, non-albuminuric, patients. This increased excretion of glycosaminoglycans in diabetic nephropathies, shown also by Partasarathy N. et al., Diabetes, 31, 738, (1982), recently suggested to Gambaro G. et al., Metabolism, 38, 419, (1989), the possibility of resorting to the determination of the amount of glycosaminoglycans excreted by urinary route as an analytical method more reliable than the microalbuminuria in the recognition of the nephropathy of diabetic origin.

Lastly, Diamond J. R. et al., Renal Physiol., 9, 366, (1986) and Parkerson M. B. et al., J. Clin. Invest., 81, 69, (1988), showed in animals the potential protective effect of heparin and its derivatives in models of experimental nephropathy not related to diabetic nephropathy, like chronic nephrosis from aminoglycosides and renal pathologies resulting from the subtotal renal ablation in the rat.

Pharmacological studies that show a possible role of exogenous glycosaminoglycans administered for prevention or therapy of diabetic glomerulopathy and diabetic nephropathy do not exist yet.

One object of the present invention is to provide a method for the prevention and therapy of diabetes nephropathy by the administration of an effective amount of a glycosaminoglycan, particularly of heparin and its derivatives obtained by depolymerization or by other chemical modifications like, for instance, O and-/or N sulfation or desulfation, of the heparinic structure, of dermatan sulfate and its low molecular weight fractions.

Another object of the present invention is to provide a method for the therapy of diabetes neuropathy by the administration of an effective amount of a glycosaminoglycan, particularly of heparin and its derivatives obtained by depolymerization or by other chemical modifications like, for instance, O and/or N sulfation or desulfation, of the heparinic structure, of dermatan sulfate and its low molecular weight fractions.

Diabetic neuropathy is a disease that hits the nerves and the neurons of the peripheral nervous system of diabetic patients. This pathology is characterized by a progressive morphofunctional alteration of this system that starts with a reduced functioning of the nerves, noticeable by a lowered speed of conduction of the nervous impulse, and that gradually proceeds up to the degeneration of the nerves and the atrophy of the neurons. This event causes a gradual loss of the sensory capacities (pain, warmth etc.), a decrease of the muscolar strength and a serious degeneration of the autonomic nervous system. This latter complication is surely the most frequent among the complications caused by diabetes; as a matter of fact about 70%-80% of the diabetic patients suffers from gastrointestinal disorders caused by the bad functioning and the degeneration of the autonomic enteric system.

This complication is directly related to the degeneration of two intrinsec neuron factors of the intestinal wall. They are the system containing Met-Enkephalin and that containing Substance P. Met-Enkephalin controls the contraction of the sphincter between stomach and intestine and moreover is able to modulate the excitability of the other enteric neurons. Substance P is contracting, therefore it is one of the substances responsible for the intestinal motility.

Di Giulio A. M. et al., J. Neurosc. Res., 24, 355-61, (1989), recently demonstrated that these two neuron systems degenerate, with loss of Substance P and Met-Enkephalin in the intestinal zones of duodenum and jejunum, in the experimental diabetes caused by alloxan.

No bibliography exists up to now related to a possible implication of endogenous glycosaminoglycans in setting up the diabetic neuropathy and moreover pharmacological studies that show a possible role of the exogenous glycosaminoglycans administered with a prophylactic or therapeutic purpose in the neuropathy of diabetic origin do not exist.

DETAILED DESCRIPTION OF THE INVENTION

The object of the present invention is the manufacture of a medicine for the use of glycosaminoglycans in the prevention and treatment of some diabetic pathologies that hit the renal system and the peripheral nervous system, particularly the pathologies known under the name of diabetic nephropathy and diabetic neuropathy.

The evaluation of the capability of glycosaminoglycans to prevent and treat these pathologies has been carried out by means of pharmacological tests on male albino rats made diabetic by treatment with streptozotocin or alloxan. The measure of the glomerular anionic charges, the measure of the thickness of the basal glomerular membrane and the evaluation of albuminuria during 24 hours in rats made diabetic with streptozotocin in comparison with some diabetic rats treated with three different kinds of glycosaminoglycans and with non-diabetic rats, were the tests carried out for diabetic nephropathy. These tests were selected because the thickening of the basal glomerular membrane and the decrease of the glomerular anionic charges, the result of a trouble of glycosaminoglycans metabolism, are elements that characterize the diabetic glomerulopathy and because such alterations can form the pathological base of the proteinuric renal syndromes typical of the diabetic nephropathy determinable through the measure of albuminuria during 24 hours.

Parameters like the measure of the levels of Met-Enkephalin and Substance P in some intestinal zones, like duodenum and jejunum, of rats made diabetic with alloxan in comparison with the same diabetic rats treated with three different kinds of glycosaminoglycans and with the non-diabetic rats treated or not with the same three different kinds of glycosaminoglycans, were examined for the evaluation of the effectiveness of glycosaminoglycans towards diabetic neuropathy.

As a matter of fact, Substance P and Met-Enkephalin are an index of the degeneration of the enteric neurons caused by diabetic neuropathy produced by the experimental diabetes from alloxan. In fact Di Giulio A. M. et al., J. Neurosc. Res., 24, 355-61, (1989) showed an alteration of the gastroenteric innervation, which is a serious symptom of diabetic neuropathy, in the chronic experimental diabetes. Because of this alteration, the content of Substance P and Met-Enkephalin decreases significantly in many intestinal zones. The lowering of Substance P and Met-Enkephalin can be quantized and therefore the effect of the pharmacological treatment can be determined with great accuracy, by means of a radioimmunoassay with specific antibodies described by Di Giulio A. M. et al., Brain Res., 342, 405-8, (1985).

The pharmacological tests for the determination of the therapeutic effectiveness of glycosaminoglycans in the treatment of diabetic nephropathy and diabetic neuropathy, carried out on groups of male albino rats, are described in detail in two examples that illustrate the invention without limiting it. These tests clearly show the achievement of the object of the present invention because the values of the parameters related to the diabetic rats treated with glycosaminoglycans correspond to the values of the non-diabetic control rats and therefore they are normal, while the values of the parameters related to the diabetic rats not treated with glycosaminoglycans show significant differences that fully document the serious pathological condition of the experimental animals.

In particular, the urinary excretion of albumin during 24 hours, albuminuria, is extremely higher in the diabetic rats not treated with glycosaminoglycans, seven times higher on average in comparison with the control rats, while it does not show any statistically significant differences in the diabetic rats treated with glycosaminoglycans. The thickness of the basal glomerular membrane analogously increases in statistically significant way and the density of the anionic charge decreases in statistically significant way in the untreated diabetic rats in comparison with the non-diabetic control rats, while no statistically significant difference is detectable among the control rats and the diabetic rats treated with glycosaminoglycans.

Finally, the experimental data related to the contents of Substance P and Met-Enkephalin in the intestinal zone show a statistically significant decrease of Substance P and Met-Enkephalin in the duodenum and the jejunum of the untreated diabetic rats in comparison with the control rats, while the treatment with glycosaminoglycans keeps statistically unchanged both the level of Substance P and that of Met-Enkephalin.

All the glycosaminoglycans can be advantageously used within the present invention, in particular those already used in the therapeutic field like heparin and its pharmaceutically acceptable salts, low molecular weight heparins obtained by chemical or enzymatic depolymerization, chemically modified heparins, for instance through reactions of O and/or N sulfation or desulfation, dermatan sulfate and its low molecular weight fractions obtained, for instance, by chemical or enzymatic depolymerization are preferred. The sodium, calcium, potassium and magnesium salts of heparin, the low molecular weight heparins obtained according to the method of chemical depolymerization described in European Patent EP 0121067. This patent application describes oligosaccharide fractions of average molecular weight 3000-6000 Daltons obtained from commercial heparin in the presence of cupric acetate, hydrogen peroxide and ascorbic acid, at a temperature of 40°-50° C. and at a pH of 7.5-8. The heparin derivatives chemically modified in basic medium described in European Publications EP 0347588 and EP 0380943, EP 0347588 correspond to U.S. Pat. No. 5,010,063 and U.S. Pat. No. 5,104,860 respectively. U.S. Pat. No. 5,010,063 describes heparin derivatives exhibiting new signals at about 53 and 54 p.p.m. in the $^{13}$C-NMR, with specific rotatory power $[\alpha]^{20}$ between about +50° and about +90°, obtained by treating the heparinic material with a base at a temperature between 35° and 60° C. followed by percolation through an ion exchange resin or dialysis and precipitation at about a neutral pH.

U.S. Pat. No. 5,104,860 describes heparin derivatives having a $^{13}$C-NMR spectrum in the zone between 102 and 92 p.p.m. exhibiting characteristic signal at about 101.3 p.p.m., a specific rotatory power at 546 nm between about +15° and about 40° in aqueous solution, a sulfur content between about 6% and about 9%, a sulfate/carboxyl ratio between about 1.20 and about 1.70 and a free amino group content between about 0.4% and about 2.1%. The process of preparation consists of reacting an aqueous solution containing a commercial, purified or low molecular weight heparin, with a 0.01N-1N solution of an alkali or alkaline earth metal base for a period of time between about 0.5 and about 24 hours at a temperature between 75° C. up to the boiling temperature of the reaction mixture, and isolating the heparin derivative from the reaction mixture. The dermatan sulfate and the low molecular weight dermatan sulfate obtained according to the method of the chemical depolymerization described in International Publication (PCT) WO 86/06729 are particularly preferred in the fulfillment of the present invention. (PCT) WO 86/06729 describes low molecular weight dermatan sulfates of molecular weight between 3500 and 8000 Daltons obtained by depolymerization of heparin and other natural polysaccharides in aqueous solution at a temperature between 20° and 70° C. in the presence of $Cu^{++}$, $Fe^{++}$, $Cr^{+++}$, $Cr_2O_7$ as a catalyst, the reaction being initiated by a peroxide or a per acid. There glycosaminoglycans can be administered through medicines suitable both for the classic administration routes like the intramuscular or intravenous route and for other routes like those subcutaneous, transdermal, iontophoretic or oral in the prevention and treatment of diabetic nephropathy and diabetic neuropathy.

The glycosaminoglycans used in the two examples that illustrate the invention without limiting it are the low molecular weight heparin obtained according to the process of chemical depolymerization described in European Patent EP 0121067, having an average molecular weight equal to 4500±1000 Daltons, the low molecular weight dermatan sulfate obtained according to the process of chemical depolymerization described in International Publication (PCT) WO 86/06729, having an average molecular weight equal to 5500±1350 Daltons, and a heparin derivative chemically modified in basic medium obtained according to the process described in European Publication EP 0380943.

EXAMPLE 1

Experimental treatment of diabetic nephropathy with glycosaminoglycans

Diabetes was induced by administering an aqueous physiological solution containing 35 mg of streptozotocin for each kilogram of body weight by intravenous route to 12 male albino Sprague-Dawley rats 7 weeks old coming from the Charles River farm in Como. Three male albino Sprague-Dawley rats having the same age and origin, which were injected with a physiological solution without streptozotocin, were the controls.

The treatment with streptozotocin caused diabetes in all the treated rats as demonstrated by glycosuria constantly higher than 1000 mg/dl. During the entire time of the experimentation, the animals were fed ad libitum by means of a standard diet based on Altromin ® of the firm Riefer of Bolzano, having a protein content equal to 20%. A week after induction of diabetes by means of streptozotocin, the 12 diabetic rats were divided into four groups of three:

GROUP A—Control diabetic rats;
GROUP B—Diabetic rats treated with low molecular weight heparin;
GROUP C—Diabetic rats treated with low molecular weight dermatan sulfate;
GROUP D—Diabetic rats treated with a heparin derivative chemically modified in basic medium.

The three non-diabetic rats were the control GROUP E.

During a period of eight months, five days a week, the diabetic rats of GROUP B were treated with 6 mg/kg/die of low molecular weight heparin administered by subcutaneous route in 1 ml of physiological solution, the diabetic rats of GROUP C with 15 mg/kg/die of low molecular weight dermatan sulfate and the diabetic rats of GROUP D with 15 mg/kg/die of heparin derivative chemically modified in basic medium, according to the same manner. A physiological solution without any active principle was contemporaneously administered, under cutis, with the same procedure, to the diabetic rats of GROUP A and to the control rats of GROUP E.

The weight of the animals was controlled once a month and the rats were stabled during 24 hours in single cages for the determination of the diuresis.

During this period of eight months, all the diabetic rats turned out to be under weight in comparison with the healthy controls and showed strong hyperglycemia, polyuria, glycosuria and acidic urines together with ketonuria so showing the dismetabolic condition.

Eight months after induction of diabetes, the animals were submitted to the 24 hours diuresis for the determination of albuminuria and then were submitted to laparatomy.

The abdominal aorta was isolated, a suture thread was passed under it by way of a slip-knot over the renal arteries and then a second thread was passed underneath. A small catheter made of polyethylene was introduced into the aorta under the second slip-knot pushing it up to the level of the renal artery where it was fixed by clasping the lower slip-knot. Subsequently, after having cut the renal veins and clasped the upper slip-knot, a solution containing 0.2% of red ruthenium in Karnowski's fixative was continuously installed by means of a pump, under a pressure of 100 mm of mercury.

Afterwards the kidney was taken out and the renal capsule was unfolded and the parenchyma was opened as a page of a book up to the pelvis by means of a lengthwise cut along the great curve. Two fragments having a side not less than $1 \div 2$ mm were taken from the cortex and were soaked for 20 hours at room temperature in the Karnowski's fixative containing 0.2% of red ruthenium. Subsequently, the cortex' takings were twice washed with cacodylate buffer and then submitted to the post-fixation treatment for one hour at room temperature in aqueous solution containing 1% of osmium tetroxyde and 0.05% of red ruthenium. Afterwards the takings were dehydrated first putting them in ethyl alcohol and then in propylene oxide. The so obtained small blocks of tissue were embedded in Epon and cut with the ultramicrotome to examine through the electronic microscopy the thickness of the basal glomerular membrane and the number of anionic charges displayed by the treatment with red ruthenium.

Photographies at 35,000 enlargements were carried out for the morphometric evaluation and the mean thickness of the basal glomerular membrane was measured.

By using a semi-automatic image analyzer Ibas Kontron, the length of the external surface of the basal glomerular membrane was measured and the number of the anionic charges displayed by the treatment with red ruthenium was counted, relating said number to 1000 nm. The statistical evaluation of the means among the groups of rats was carried out with the non-parametric test of Wilcoxon F., described in "Individual comparison by ranking methods", Biometr. Bull., 1, 80-3, (1945), at the significance threshold $p=0.05$.

The experimental data related to the thickness of the basal membrane, to the number of the glomerular anionic charges and to albuminuria are reported in the following table 1.

TABLE 1

| GROUPS OF RATS | Glomerular anionic charges (number/1000 nm) $X \pm s.e.$ | Thickness of the basal membrane (nm) $X \pm s.e.$ | Albuminuria (µg/die) $X \pm s.e.$ |
|---|---|---|---|
| A | 22.17 ± 4.20 | 375 ± 127 | 318.67 ± 31.34 |
| B | 43.43 ± 3.25 | 238 ± 39.89 | 21.20 ± 5.21 |
| C | 36.47 ± 6.54 | 265 ± 21.94 | 56.67 ± 36.65 |
| D | 40.97 ± 5.18 | 221 ± 33.15 | 30.56 ± 9.77 |
| E | 38.53 ± 1.61 | 235 ± 15.89 | 45.63 ± 25.42 |

The experimental data reported in table 1 clearly show that the diabetic rats not treated with glycosaminoglycans (GROUP A) undergo serious morphological anomalies, strong thickening of the basal membrane and remarkable decrease of the glomerular anionic charges, which, consequently, go with a very evident clinical anomaly shown by values of albuminuria even seven times higher than those of the control rats (GROUP E).

On the contrary, the diabetic rats treated with low molecular weight heparin (GROUP B), the diabetic rats treated with low molecular weight dermatan sulfate (GROUP C) and the diabetic rats treated with a heparin derivative chemically modified in basic medium (GROUP D), show values both of the morphologic parameters and of the clinical parameter in agreement with the data of the group of the non-diabetic control rats (GROUP E).

Therefore the treatment with glycosaminoglycans like the low molecular weight heparin, the low molecular weight dermatan sulfate and the heparin derivative chemically modified in basic medium, is able to cause remarkable morphological and clinical improvements in the experimental model of diabetic nephropathy caused by streptozotocin in the rat. As a matter of fact, the capability of glycosaminoglycans to prevent diabetic nephropathy is clearly demonstrated by the lack of thickening of the basal glomerular membranes and of the decrease of the glomerular anionic charges and by the inhibition of the appearance of albuminuria.

EXAMPLE 2

Experimental treatment of diabetic neuropathy with glycosaminoglycans

Diabetes was induced by means of a subcutaneous injection of alloxan dissolved in a pH 3 citrate-phosphate buffer at the dosage of 100 mg for each kilogram of body weight, in male albino Sprague-Dawley rats weighing 250 g coming from the Charles River farm in Como. The appearance of diabetes was ascertained a week after the treatment with alloxan by determining glycosuria with the Glucur Test of Boehringer Biochemia and the glycemia by means of the hexokinase method with the Gluco-Quant of Boehringer Biochemia. Only the diabetic rats having a value of glycemia higher than 400 mg/dl and a body weight lower than 320 g were used for the experimentation. Male albino Sprague-Dawley rats having the same age and weight and treated with a subcutaneous injection of citrate-phosphate buffer alone were used as non-diabetic control rats.

Both diabetic and control rats were stabled and fed in the same manner, with water and food ad libitum.

The diabetic rats were divided into four groups of 12:
GROUP A—Control diabetic rats;
GROUP B—Diabetic rats treated with low molecular weight heparin;
GROUP C—Diabetic rats treated with low molecular weight dermatan sulfate;
GROUP D—Diabetic rats treated with a heparin derivative chemically modified in basic medium.

Also the non-diabetic control rats were divided into four groups of 12:
GROUP E—Non-diabetic control rats;
GROUP F—Non-diabetic rats treated with low molecular weight heparin;
GROUP G—Non-diabetic rats treated with low molecular weight dermatan sulfate;
GROUP H—Non-diabetic rats treated with heparin derivative chemically modified in basic medium.

During a period of time of 18 weeks, groups B and F were treated with 6 mg/kg/die of low molecular weight heparin administered by subcutaneous route in 1 ml of physiological solution, groups C and G with 15 mg/kg/die of low molecular weight dermatan sulfate and groups D and H with 15 mg/kg/die of heparin derivative chemically modified in basic medium, in the same manner, for 5 days a week, starting from the week following that of the induction of diabetes with alloxan. A physiological solution without any active principle was contemporaneously administered under cutis in the same manner to the control diabetic rats of group A and to the control non-diabetic rats of group E.

All the animals were fasted for 24 hours and then were killed by decapitation at the end of the 18 weeks of treatment. The intestine was dissected in segments; the duodenum and the jejunum were isolated, carefully washed with Krebs solution cooled to about 0° C. and lastly dissected in 5 mm long pieces.

These specimens were frozen at −30° C. with liquid nitrogen till the moment of carrying out the radioimmunoassays for the determination of Substance P and Met-Enkephalin that were determined by using specific immunizing sera as described by Di Giulio A. M. et al., Brain Res., 342, 405-8, (1985).

The experimental data, expressed as mean (X) ± standard error (s.e.), related to the levels of Substance P and Met-Enkephalin, measured as ng/mg protein, in the duodenum and the jejunum of the experimental animals, are reported in the following tables 2 and 3.

TABLE 2

| GROUPS OF RATS | LEVELS OF SUBSTANCE P | |
|---|---|---|
| | Amount of Substance P in the duodenum (ng/mg protein) X ± s.e. | Amount of Substance P in the jejunum (ng/mg protein) X ± s.e. |
| A | 0.28 ± 0.024 | 0.30 ± 0.018 |
| B | 0.41 ± 0.021 | 0.38 ± 0.016 |
| C | 0.38 ± 0.060 | 0.51 ± 0.018 |
| D | 0.43 ± 0.019 | 0.44 ± 0.028 |
| E | 0.40 ± 0.025 | 0.37 ± 0.023 |
| F | 0.42 ± 0.011 | 0.36 ± 0.022 |
| G | 0.33 ± 0.025 | 0.36 ± 0.014 |
| H | 0.39 ± 0.045 | 0.41 ± 0.036 |

TABLE 3

| GROUPS OF RATS | LEVELS OF MET-ENKEPHALIN | |
|---|---|---|
| | Amount of Met-Enkephalin in the duodenum (ng/mg protein) X ± s.e. | Amount of Met-Enkephalin in the jejunum (ng/mg, protein) X ± s.e. |
| A | 0.037 ± 0.037 | 0.50 ± 0.041 |
| B | 0.14 ± 0.009 | 0.88 ± 0.021 |
| C | 0.09 ± 0.018 | 0.80 ± 0.038 |
| D | 0.15 ± 0.021 | 0.85 ± 0.033 |
| E | 0.19 ± 0.013 | 0.90 ± 0.031 |
| F | 0.17 ± 0.015 | 0.93 ± 0.022 |
| G | 0.18 ± 0.009 | 0.80 ± 0.028 |
| H | 0.16 ± 0.008 | 0.87 ± 0.043 |

The experimental data clearly show that the levels (in ng/mg protein) of both Substance P and Met-Enkephalin in the duodenum and the jejunum of the untreated diabetic animals (Group A) are significantly lower than those found in the corresponding organs of the healthy control animals (group E). This decrease of Substance P and Met-Enkephalin is prevented by the pharmacological treatments with glycosaminoglycans (groups B, C and D). As a matter of fact, the data of the groups B, C and D do not show any significant difference in comparison with the control group E. Moreover, the results obtained with the groups F, G and H, i.e. with the non-diabetic animals treated with glycosaminoglycans, clearly show that the administration of glycosaminoglycans does not significantly change the content of substance P and Met-Enkephalin in the healthy animals. This fact shows that the pharmacological effect of glycosaminoglycans occurs only on the cause of the neuropathy and not on the synthesis of Substance P and Met-Enkephalin in the healthy animals.

Moreover, the effect of normalization by the glycosaminoglycans on substance P and Met-Enkephalin in the diabetic animals goes with a concomitant maintenance of levels of glycemia equal to those of the normal not diabetic rats. Therefore all these experimental data show that glycosaminoglycans are active in the inhibition of the experimental diabetic neuropathy, a fact that justifies the claim of the use of the glycosaminoglycans in the prevention and treatment of diabetic neuropathy.

We claim:

1. A method of treatment of diabetic nephropathy which consists of administering to a living subject affected by diabetic nephropathy, said living subject exhibiting prior to treatment, thickening of the basal membrane, decrease of the glomerular anionic charges and high albuminuria when compared with non-diabetic subjects, an effective amount of a member selected from the group consisting of low molecular weight heparin derivatives obtained by chemical or enzymatic depolymerization, chemically modified heparin derivatives and low molecular weight dermatan sulfates obtained by chemical or enzymatic depolymerization.

2. The method according to claim 1 wherein said low molecular weight heparin derivatives are obtained from commercial heparin in the presence of cupric acetate, hydrogen peroxide and ascorbic acid, at a temperature of 40°–50° C. and at a pH of 7.5–8.

3. The method according to claim 1 wherein the chemically modified heparin derivatives exhibit new signals at about 53 and 54 p.p.m. in the $^{13}$C-NMR, with specific rotatary power $[\alpha]^{20}$ between about +50° and about +90° and are obtained by a) treating the heparinic material with a base at a temperature between 35° and 60° C., followed by percolation through an ion exchange resin or dialysis and precipitation at about a neutral pH or b) are heparin derivatives having a $^{13}$C-NMR spectrum in the zone between 102 and 92 p.p.m. exhibiting characteristic signal at about 101.3 p.p.m., a specific rotary power at 546 nm between about +15° and about +40° in aqueous solution, a sulfur content between about 6% and about 9%, a sulfate/carboxyl ratio between about 1.20 and 1.70 and a free amino group content between about 0.4% and 2.1% prepared by reacting an aqueous solution containing a commercial, purified or low molecular weight heparin, with a 0.01N–1N solution of an alkali or alkaline earth metal base for a period of time between about 0.5 and about 24 hours at a temperature between 75° C. up to the boiling temperature of the reaction mixture, and isolating the heparin derivative from the reaction mixture.

4. The method according to claim 1 wherein the low molecular weight dermatan sulfate has a molecular weight between 3500 and 8000 Daltons and is obtained by depolymerization of heparin and other natural polysaccharides in aqueous solution at a temperature between 20° and 70° C. in the presence of $Cu^{++}$, $Fe^{++}$, $Cr^{+++}$, $Cr_2O_7^-$ as a catalyst, the reaction being initiated by a peroxide or a peracid.

5. A method of treatment of diabetic neuropathy which consists of administering to a living subject affected by diabetic neuropathy an effective amount of a member selected from the group consisting of low molecular weight heparin derivatives obtained by chemical or enzymatic depolymerization, chemically modified heparin derivatives, and low molecular weight dermatan sulfates obtained by chemical or enzymatic depolymerization, said living subject exhibiting prior to treatment decrease of Substance P and decrease of Met-Enkephalin in the duodenum and jejunum when compared with non-diabetic subjects.

6. The method according to claim 5 wherein said low molecular weight heparin derivatives are obtained from commercial heparin in the presence of cupric acetate, hydrogen peroxide and ascorbic acid, at a temperature of 40°–50° C. and a pH of 7.5–8.

7. The method according to claim 5 wherein the chemically modified heparin derivatives exhibit new signals at about 53 and 54 p.p.m. in the $^{13}$C-NMR, with specific rotatory power $[\alpha]^{20}$ between about +50° and about +90° and are obtained a) by treating the heparinic material with a base at a temperature between 35° and 60° C., followed by percolation through an ion exchange resin or dialysis and precipitation at about a neutral pH or b) are heparin derivatives having a $^{13}$C-NMR spectrum in the zone between 102 and 92 p.p.m. exhibiting characteristic signal at about 101.3 p.p.m., a specific rotatory power at 546 nm between about +15° and about +40° in aqueous solution, a sulfur content between about 6% and about 9%, a sulfate/carboxyl ratio between about 1.20 and 1.70 and a free amino group content between about 0.4% and about 2.1% prepared by reacting an aqueous solution containing a commercial, purified or low molecular weight heparin with a 0.01N–1N solution of an alkali or alkaline earth metal base for a period of time between about 0.5 and about 24 hours at a temperature between 75° C. up to the boiling temperature of the reaction mixture, and isolating the heparin derivative from the reaction mixture.

8. The method according to claim 5 wherein the low molecular weight dermatan sulfate has a molecular weight between 3500 and 8000 Daltons and is obtained by depolymerization of heparin and other natural polysaccharides in aqueous solution at a temperature betwen 20° and 70° C. in the presence of $Cu^{++}$, $Fe^{++}$, $Cr^{+++}$, $Cr_2O_7^-$ as a catalyst, the reaction being initiated by a peroxide or a peracid.

* * * * *